(12) United States Patent
Quint et al.

(10) Patent No.: US 9,891,158 B2
(45) Date of Patent: Feb. 13, 2018

(54) METHOD FOR DETECTING PARTICLES

(71) Applicant: Fraunhofer-Gesellschaft zur Förderung der angewandten Forschung e.V., München (DE)

(72) Inventors: Stephan Quint, Dortmund (DE); Michael Baβler, Mainz (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

(21) Appl. No.: 14/896,331

(22) PCT Filed: May 28, 2014

(86) PCT No.: PCT/EP2014/061060
§ 371 (c)(1),
(2) Date: Dec. 4, 2015

(87) PCT Pub. No.: WO2014/195207
PCT Pub. Date: Dec. 11, 2014

(65) Prior Publication Data
US 2016/0123863 A1 May 5, 2016

(30) Foreign Application Priority Data
Jun. 7, 2013 (DE) .................. 10 2013 105 953

(51) Int. Cl.
*G01N 15/14* (2006.01)
(52) U.S. Cl.
CPC ..... *G01N 15/1429* (2013.01); *G01N 15/1434* (2013.01); *G01N 2015/1447* (2013.01)
(58) Field of Classification Search
CPC ............................................... G01N 15/1429
See application file for complete search history.

(56) References Cited

U.S. PATENT DOCUMENTS

| | | | |
|---|---|---|---|
| 5,414,428 A * | 5/1995 | Gallagher et al. | ............ 342/132 |
| 5,786,788 A | 7/1998 | Schober et al. | |

(Continued)

FOREIGN PATENT DOCUMENTS

| | | |
|---|---|---|
| DE | 10 2012 210 289 A1 | 12/2013 |
| EP | 2 211 164 A1 | 7/2010 |

OTHER PUBLICATIONS

Adly T. Fam et al, "Multiplicative Mismatched Filter for Optimum Sidelobe Suppression in Barker Codes", Proc. of SPIE, vol. 6235, May 2006, pp. 62351M-1-62351M-10.

(Continued)

*Primary Examiner* — David Porta
*Assistant Examiner* — Hugh H Maupin
(74) *Attorney, Agent, or Firm* — Drinker Biddle & Reath LLP

(57) ABSTRACT

The present invention concerns a method of detecting particles which move along a trajectory and which produce or at least influence electromagnetic radiation, an electrical field or a magnetic field, wherein the electromagnetic radiation, the electrical field or the magnetic field is detected, in which a structuring device is used, which either ensures that the particles along the trajectory produce or at least influence electromagnetic radiation, an electrical field or a magnetic field substantially only at non-periodic spatial spacings, or ensures that the electromagnetic radiation, the electrical or the magnetic field is detected substantially only at non-periodic spatial spacings along the trajectory. To provide a method of detecting particles which move along a trajectory and which produce or at least influence electromagnetic radiation, an electrical field or a magnetic field, it is proposed according to the invention that the detected signal S is processed by means of a mismatched filter $F_1$ and if the signal $D_{F_1}(S)$ filtered in that way fulfils a predefined thresh- (Continued)

Figure 1:
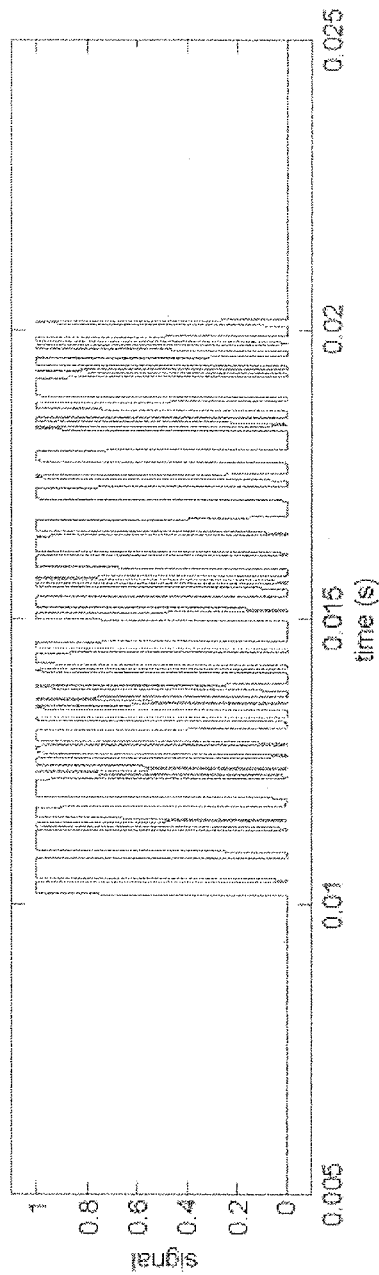

old criterion a particle is detected and if the signal filtered in that way does not fulfill the predefined threshold criterion no particle is detected.

16 Claims, 15 Drawing Sheets

(56) References Cited

U.S. PATENT DOCUMENTS

| | | | |
|---|---|---|---|
| 7,782,235 B1* | 8/2010 | Velazquez | H03M 1/1004 341/118 |
| 2008/0068605 A1 | 3/2008 | Herzog et al. | |
| 2010/0201988 A1 | 8/2010 | Kiesel et al. | |
| 2011/0222062 A1* | 9/2011 | Martini et al. | 356/417 |

OTHER PUBLICATIONS

Peter Kiesel et al., "Spatially modulated fluorescence emission from moving particles", Applied Physics Letters, vol. 94, No. 4, 2009, pp. 041107-1-041107-3.

Hermann Rohling et al., "Mismatched-Filter Design for Periodical Binary Phased Signals", IEEE Transactions on Aerospace and Electronic Systems, vol. 25, No. 6, Nov. 1989, pp. 890-897.

Hermann Rohling, "Radar CFAR Thresholding in Clutter and Multiple Target Situation", IEEE Transactions on Aerospace and Electronic Systems, vol. AES-19, No. 4, Jul. 1983, pp. 608-621.

Indranil Sarkar et al., "Multiplicative Mismatched Filters for Sidelobe Suppression in Barker Codes", IEEE Transaction on Aerospace and Electronic Systems, vol. 44, No. 1, Jan. 2008, pp. 349-359.

\* cited by examiner

METHOD FOR DETECTING PARTICLES

CROSS REFERENCE TO RELATED APPLICATIONS

This application is a National Stage of International Application No. PCT/EP2014/061060 filed May 28, 2014, which claims benefit of German Patent Application No. 10 2013 105 953.8 filed Jun. 7, 2013, both of which are herein incorporated by reference in their entirety.

The present invention concerns a method of detecting particles which move along a trajectory and which produce or at least influence electromagnetic radiation, an electrical field or a magnetic field. In that case the electromagnetic radiation, the electrical field or the magnetic field is detected. In addition a structuring device is used, which either ensures that the particles along the trajectory produce or at least influence electromagnetic radiation, an electrical field or a magnetic field substantially only at non-periodic spatial spacings, or ensures that the electromagnetic radiation, the electrical or the magnetic field is detected substantially only at non-periodic spatial spacings along the trajectory.

Such a method is used for example in through-flow cytometers. In through-flow cytometry a cell suspension is passed through a through-flow measuring cell. The cell suspension is irradiated with a light source generally comprising a plurality of lasers whereby the cells to be detected or a dye bound to the cells are excited and emit fluorescence signals. A non-periodic structured mask is used as a structuring device and the particles are taken past one side of the mask at a speed v and the electromagnetic radiation passing through the mask, the electrical or the magnetic field is detected on the other side.

It will be understood however that the structuring device does not have to be a shadow mask. It would for example also be conceivable that the particles to be detected have to be excited by means of an excitation radiation to produce an electromagnetic radiation. That excitation radiation could be made available for example by means of diffractive optical elements only at non-periodic spatial spacings along the trajectory so that the electromagnetic radiation to be detected is also emitted substantially only at those locations. The structuring device then comprises the diffractive optical elements.

The present invention is described hereinafter by means of a method of detecting radiation-emitting particles. Nonetheless the method can also be employed for the detection of for example particles producing or influencing a magnetic field or an electrical field. It would also be conceivable for electromagnetic radiation to be passed through and detected by the mask so that the particles moved past same briefly attenuate or at least influence the directed electromagnetic radiation when passing the mask.

In an embodiment the time modulation of the fluorescence signal is produced by a shadow mask structured along the direction of movement of the particles. Windows in that shadow mask allow transmission of the fluorescence light and correspond to the transmission state "1". Closed region of the mask prevent transmission and correspond to the state "0", The spatial structuring of the mask is mathematically described by so-called binary sequences, a series of zeros and ones. Therefore the structured mask is also referred to as a binary mask. In principle however regions with reduced transmission to which an intermediate state of for example "½" could be attributed would also be conceivable. Even if the invention is described hereinafter using the example of binary masks structured masks with intermediate states would also be conceivable.

Those fluorescence signals are detected and evaluated to draw conclusions about the number, nature, intensity and speed of the individual particles.

Such a method is described for example in Kiesel et al, Appl. Phys. Lett. 94, 041107-1 (2009). In that case the measured signal is filtered by means of an optimum filter to achieve pulse compression and is then derived in respect of time to eliminate a possible signal offset. In the signal which then occurs a fixed threshold is used for event detection.

The detected signal is naturally unipolar as there cannot be any negative amplitudes in fluorescence emission. Strictly speaking that naturally only applies to ideal signals. In practice electronic noise under some circumstances also causes negative amplitudes. The term optimum filter is used to denote a filter which supplies a filtered signal with the greatest signal-noise ratio. For the situation of a unipolar signal such a filter always has exclusively unipolar filter coefficients. In general the optimum filter corresponds in its functional configuration to the signal to which filtering is to be implemented except for a multiplicative prefactor which can be equally applied to all coefficients.

The use of non-periodic masks or signal configurations serves to improve the signal-noise ratio and time pulse compression. It will be noted however that with such a method signal sidelobes occur in correlation signals, which markedly increases the difficulty in terms of discovery probability of weakly fluorescing objects in the presence of larger more strongly light-emitting objects.

Figure 2:
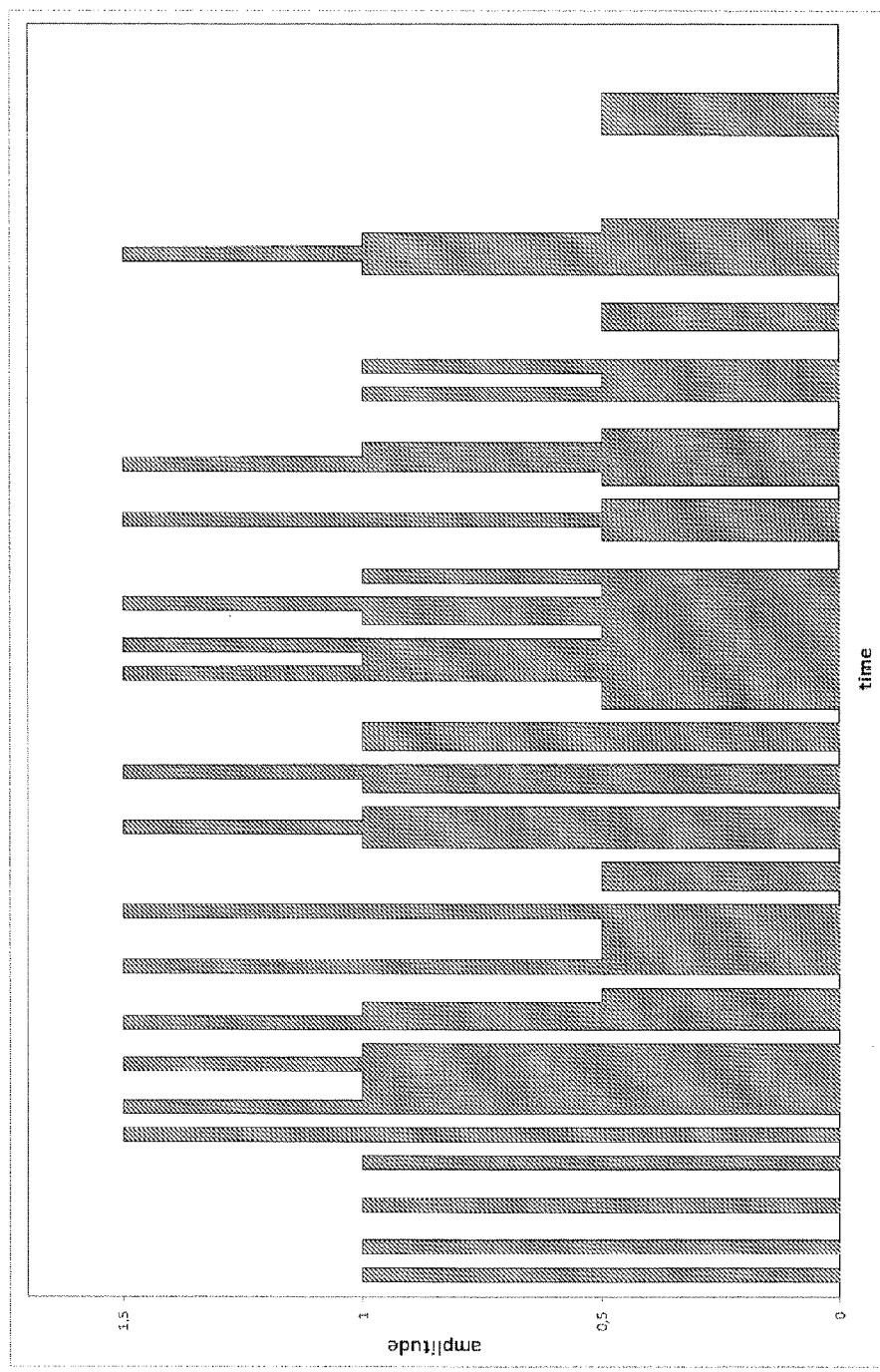

For clarification purposes reference is directed to FIGS. 1 through 4. FIG. 1 shows a diagrammatic view of a measurement signal in dependence on time without taking account of the noise and offset component. FIG. 2 shows the amplitude-modulated rectangular signals for two particles. It will be seen that the measured signals involve radiation intensities of different magnitudes. The first signal has double the amplitude of the second signal. Superposing gives a third level which assumes 1.5 times the value of the first signal. The rectangular signals for the individual particles however are not only of different amplitudes, they are also shifted in respect of time (in the X direction), that is to say the case is considered in which two particles of different light strength and different extent move shortly one after the other past the binary mask so that the total signal detected with a detector is a superpositioning of the individual signals originating from the individual particles.

Figure 3:
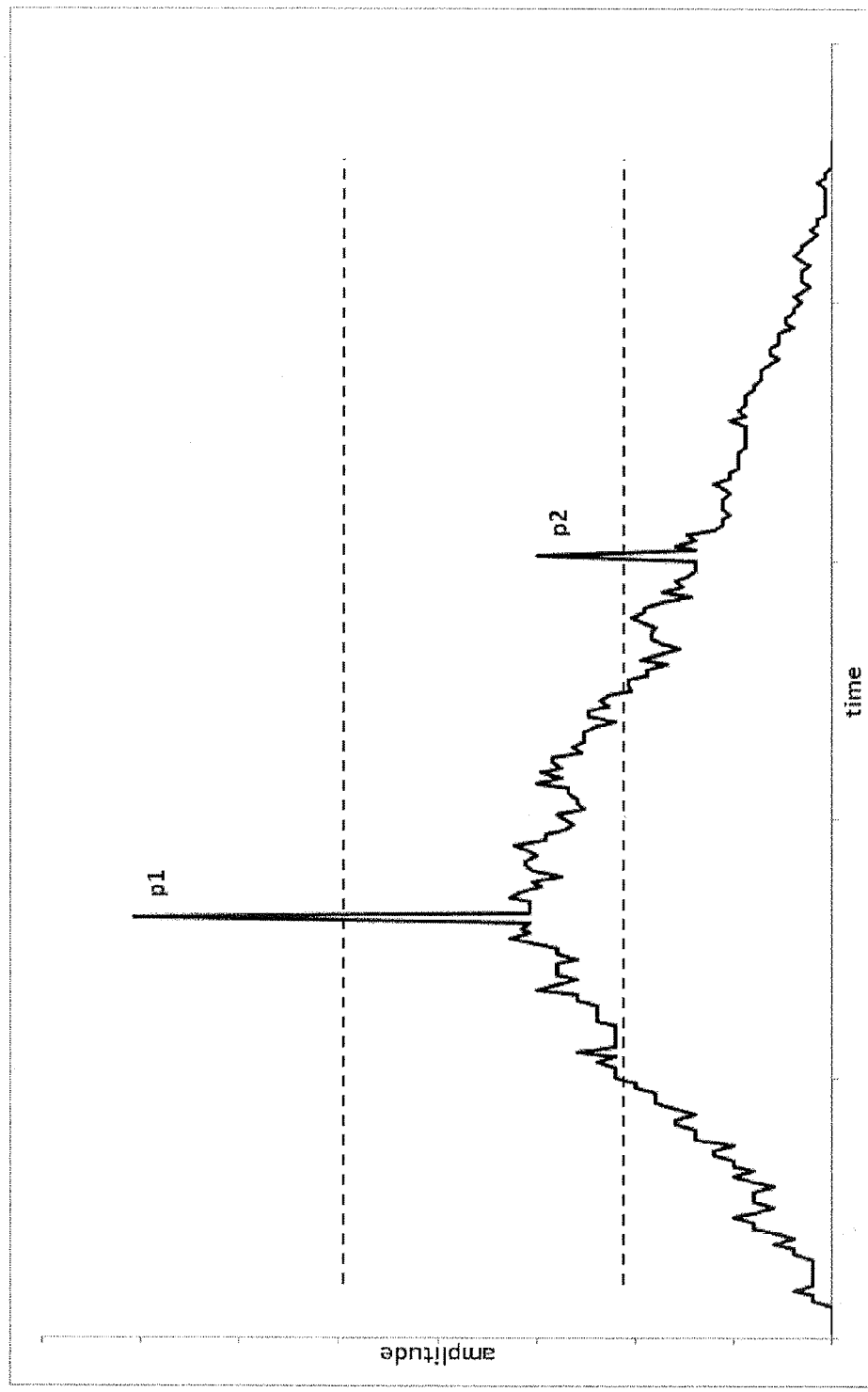

That signal is usually processed with an optimum filter, thereby giving the filtered signal shown in FIG. 3. The signal of the first particle can be clearly seen while the weaker signal of the second particle is only weakly pronounced. For automated particle detection a limit value is generally established and signals which are stronger than the established limit value are interpreted as particle detection. Particularly in the case of detecting a plurality of particles involving different signal strengths however that is not possible. By way of example two threshold values have been shown as broken lines in FIG. 3. If the greater value is used as a threshold value only the first particle is detected as the signal strength of the second particle is below the greater threshold value. If instead a threshold value is selected which is so low that the second particle is correctly identified the background signal linked to the first particle is however also above the threshold value so that the first particle is possibly wrongly counted a plurality of times.

Figure 4:
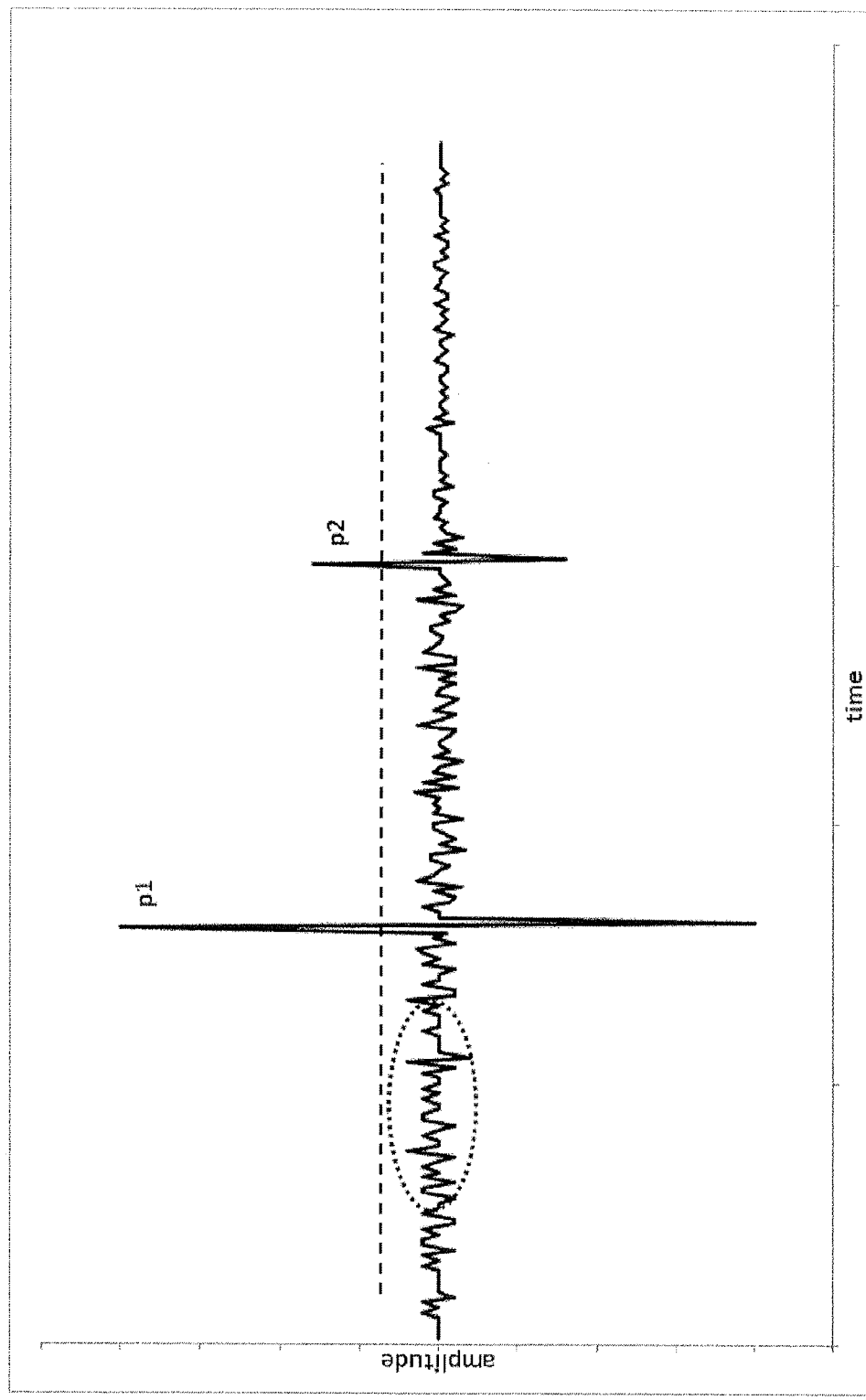

Therefore usually the filtered signal is derived in respect of time, thereby giving the signal shown in FIG. 4. The signal no longer has any offset.

Once again the signal of the first particle (p1) can be clearly seen while the signal of the second particle (p2) is only slightly greater than the signals in the sidelobes. For example a threshold value has been shown in the Figure. If the threshold value is too high the signal of the second particle is not detected. If in contrast the threshold value is too low then not only is the second particle detected, but in addition peaks of the sidelobes which are emphasized in the Figure with a dotted line are additionally wrongly detected as an event.

Due to the sidelobes of the larger or brighter object therefore in the time domain in which the sidelobes occur the lower identification threshold for further, smaller, that is to say darker, objects is lifted.

The hitherto usual fixed overall threshold value for event detection, which is applied to the correspondingly derived and prefiltered signal, therefore suffers from the disadvantage that a certain minimum signal energy, that is to say a fluorescence signal of a minimum magnitude, must be present to be able to detect an object. Particularly in the case of a wide magnitude range of objects too many incorrect detections occur due to the high sidelobe amplitudes with a threshold value which is set too low. A more highly selected threshold value makes the discovery of smaller objects against the background of the sidelobes of the larger object which emits light more strongly in the magnitude spectrum impossible.

Taking the described state of the art as the basic starting point the object of the present invention is therefore that of providing a method which is markedly improved and which can reliably detect signals of smaller objects in the time domain of the sidelobes of a larger object.

According to the invention that object is attained in that the detected signal S is processed by means of a mismatched filter $F_1$ and if the signal $D_{F1}(S)$ filtered in that way fulfils a predefined threshold criterion a particle is detected and if the signal filtered in that way does not fulfill the predefined threshold criterion no particle is detected.

The term mismatched filter is used to denote a filter which does not give the greatest signal-noise ratio in the filtered signal. As an optimum filter, that is to say a filter adapted to the greatest signal-noise ratio is only unipolar, for example has only positive filter coefficients, any filter with at least one filter coefficient with a reversed sign is a mismatched filter in accordance with this application. However filters with exclusively unipolar filter coefficients can also be mismatched filters if they are riot matched to the greatest signal-noise ratio.

More specifically it has surprisingly been found that the signal dynamic can be markedly improved if it is precisely not an optimum filter that is used, although the signal-noise ratio is worsened thereby.

Obviously a weighted multilevel filter (multilevel mismatched) can also be used. In this context a multilevel filter means that the filter coefficients may assume not only binary values (levels) but also any desired intermediate value (multilevel).

In a simple preferred case a mismatched filter can be calculated from an optimum filter by subtraction of a predetermined value (which is unequal to zero) from all filter coefficients. That reduces the offset. For the best, the predetermined value is set to the average magnitude of the filter coefficients of the optimum filter. The offset is then removed without a differentiation step.

Such an offset-correcting filter eliminates both the constant background and also the triangular configuration of the correlation signal and compresses the entire signal energy into the sharp main maximum.

The simple unipolar filter $F_j$ with $f_i=m_i>0$ is replaced by a bipolar filter having the coefficients $f_i \in \{h>0, l<0\}$.

A preferred embodiment provides that the detected signal S is processed by means of a plurality of different mismatched filters ($F_i$, i=1,2, . . . ) to produce a plurality of digitally filtered signals $D_{Fi}(S)(i=1,2, . . . )$, that a best digitally filtered signal $D_{Fbest}$ is selected from the plurality of digitally filtered signals $D_{Fi}(S)(i=1,2, . . . )$ by means of a predetermined selection criterion and if the best digitally filtered signal $D_{Fbest}$ fulfills a predefined threshold criterion a particle is detected and if the best digitally filtered signal $D_{Fbest}$ does not fulfill the predefined threshold criterion no particle is detected.

According to the invention therefore a set of different mismatched filters is provided and the detected signal is processed with the different mismatched filters and then, from the different digitally filtered signals, one is selected as the best filtered signal $D_{Fbest}$ and same is used for the event detection.

The mismatched filter $F_1$ can be adapted to a particle speed $v_1$ and to the non-periodic binary mask. For example a usual particle speed could be selected and the theoretical radiation signal could be calculated on the basis of the selected non-periodic binary mask.

In a further step the mismatched filter $F_1$ can then be so selected that the digitally filtered signal as far as possible comprises only a peak and no sidelobes. If then the particle moves at the assumed speed through the through-flow cytometer then a marked signal with severely suppressed sidelobes is achieved by virtue of the mismatched filter ascertained in that way. For such a filter therefore both a high degree of pulse compression and also a high dynamic due to an improved peak-to-sidelobe spacing is achieved.

In general however it is not possible to predict the exact speed of the particles in the through-flow cytometer. In practice there are speed variations here, which are not negligible.

As however the mismatched filter is adapted only to a specific speed, it is only when the particle involves approximately the specific speed used that a marked signal without sidelobes is obtained.

According to a preferred embodiment a plurality of mismatched filters is used, which are respectively adapted to a particle speed $v_i$, wherein each mismatched filter is adapted to another particle speed $v_j$.

If now a particle is passed at an unknown speed through the through-flow cytometer the detected signal S can be processed by means of the plurality of different digital mismatched filters to produce a plurality of digitally filtered signals. As however a marked signal with severely suppressed sidelobes is obtained only when the particle speed approximately coincides with the specific speed used in development of the mismatched filter, the various mismatched filters deliver filtered signals of differing quality, that is to say signals with a differing peak height. In general filtering with the mismatched filter delivers the best digitally filtered signal which was adapted to a particle speed $v_i$ which is closest to the actual speed v.

Thus in a preferred embodiment the speed v of the particle can be approximately determined by the speed to which the mismatched filter which leads to the best digitally filtered signal $D_{Fbest}$ is adapted is established as the particle speed.

It has been shown that preferably the length of the mismatched filter or filters must correspond at least to the length of the signal to be filtered—by means mismatched filters—and from three times the length of the signal to be filtered—by means of mismatched filters—scarcely any improvements in the peak-to-sidelobe spacing are to be observed.

| Preprocessing | Signal length after preprocessing | Minimum length mismatched filter | Optimum length of the mismatched filter | Minimum length output signal |
|---|---|---|---|---|
| Optimum filter | 2M − 1 | 2M − 1 | 3(2M − 1) | 4M − 3 |
| Optimum filter + derivation | 2M | 2M | 3 * 2M | 4M − 1 |
| None | M | M | 3M | 2M − 1 |

The Table specifies the input signal, output signal and filter lengths for the mismatched filter. In that respect M denotes the length of the detected signal. If for example a signal of a duration of 5 seconds is sampled at a sampling rate of 10/s that gives a length of 50. If that signal is passed directly to the mismatched filtering operation the mismatched filter must be of a minimum length of 50 (=M). Better results are achieved however with longer filters. A filter of a length of more than 150 (=3M) however does not give any additional improvement.

Because of the good results with moderate computing involvement the last line with an optimum mismatched length of 3M is to be preferred for most application situations.

In a further preferred embodiment the mismatched filter or the mismatched filters is or are ascertained by means of optimization of a digitally filtered test signal, wherein a signal to be expected for a particle speed $v_i$ and the binary mask used is used as the test signal. In other words the test signal is digitally filtered and the mismatched filter is optimized until the digitally filtered signal assumes an optimum form.

In a preferred embodiment the mismatched filters are ascertained by means of a maximization of the peak-to-sidelobe ratio (PSLR) or a minimization of the integrated sidelobe-to-peak ratio (ISLR) of the digitally filtered test signal. It has been shown in practice that minimization of the integrated sidelobe-to-peak ratio gives the somewhat better result. The environment of the main peak is less wavy for the ISLR as the square values of the deviations are involved in the optimization process. In the case of PSLR the largest possible positive (maximum) deflections are travel-optimized. That can then have the result that negative outliers occur, which in turn can be superposed with main peaks of other signals. In regard to optimization to ISLR the environment of the main peak appears more homogeneous.

In other words the coefficients of the mismatched filter are varied until the integrated sidelobe-to-peak ratio becomes minimal.

In a preferred embodiment a relative threshold value is used as the predetermined selection criterion.

It has been found that, in spite of the use according to the invention of mismatched filters sidepeaks can occur by virtue of interference between various filter channels. Those interferences are correspondingly greater, the greater the signal energy of a respective object. Advantageously therefore a relative threshold value is calculated to keep the false detection rate constant independently of the signal energy.

Such a method is known from radar technology and is referred there as "constant false alarm rate detection". That method however has to be adapted to the present case of particle detection.

For example the output signal of a "cell-averaging" CFAR (CACFAR), a "cell averaging greatest of" CFAR (CAGO CFAR) or an "ordered statistic" CFAR (OS CFAR) is used for detection. Examples in this respect are described hereinafter.

The above-mentioned detection procedures are described in "Radar CFAR Thresholding in Clutter and Multiple Target Situations", Hermann Rohling, IEEE Transactions on Aerospace and electronic Systems, Vol. AES-19, No. 4, July 1983.

In a further preferred embodiment it is provided that $v_i$ is selected as $<v_{i+1}$, that a subgroup of mismatched filters ($F_i=(k+c \times i)$ with a constant k and a factor c is selected from the plurality of different mismatched digital filters ($F_i$, i=1, 2, . . . ) and the detected signal S is processed by means of the subgroup of different mismatched filters ($F_i$, i=1, 2, . . . ) to produce a plurality of digitally filtered signals $D_{Fi}(S)(i=1,2, \ldots )$. A best digitally filtered signal $D_{Fbest}$ is selected from the plurality of digitally filtered signals $D_{Fi}(S)(i=1,2, \ldots )$ by means of a predetermined selection criterion. In a further step a further subgroup of digital mismatched filters ($F_i$, i(best−c . . . best+c) is selected, whose elements were ascertained on the basis of particle speeds which are in a predetermined interval around the particle speed to which the selected best mismatched filter was adapted. The processing step and the selection step are then again carried out using the further subgroup and if the best digitally filtered signal $D_{Fbest}$ fulfills a predefined threshold criterion a particle is detected and if the best digitally filtered signal $D_{Fbest}$ does not fulfill the predefined threshold criterion no particle is detected.

Particularly when the resolution of the method according to the invention is to be further increased a large number of different mismatched filters must be used, which are respectively adapted to different particle speeds. If for example particle speeds of between 3 and 6 m/s are to be reckoned upon, mismatched filters for the speeds 3, 3.1, 3.2, . . . , 5.8, 5.9 and 6 m/s could be used. It will be noted however that then the detected signal must be processed in parallel with 31 different mismatched filters, which greatly increases the necessary computing power.

According to an embodiment therefore that computation is initially performed only for a subgroup of the mismatched filters. In the stated example for example the digital filtering operation could firstly be effected by means of the mismatched filters adapted to the speeds 3, 4, 5 and 6 m/s. If it is now shown here for example that the mismatched filter adapted to the speed of 4 m/s shows the best result the signal is again filtered with a subgroup of digital mismatched filters which for example are adapted to the speeds 3.5, 3.6, 4.0, . . . 4.4, 4.5 m per second. The best digital signal is then again selected to implement event detection. Therefore the described method firstly involves a kind of coarse rastering and as soon as the speed range in which the actual particle speed is to be found was determined fine rastering is performed in that range. That reduces the computation involvement for this example from initially 31 to 4+11=15 channels.

Alternatively thereto a known functional configuration (for example quadratic) could be adapted to the coarse rastering (fit) to find the maximum.

In some situations of use it may be advantageous if the detected signal is initially prefiltered with an optimum filter and then further processed with a mismatched filter. In many situations of use it may also be advantageous if the signal prefiltered by optimum filter is derived in respect of time and then processed with the mismatched filter. In principle however both the functions of the optimum filter and also the derivation in respect of time can be implemented by the mismatched filter.

Figure 5:
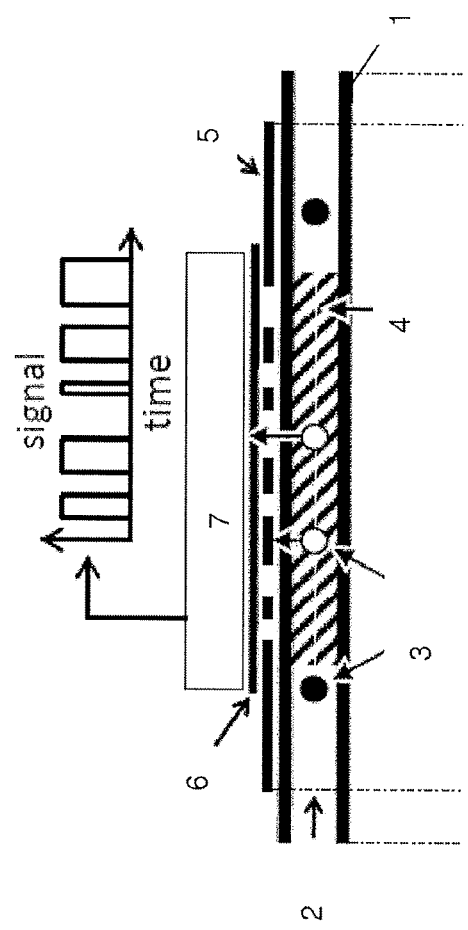
Figure 6:
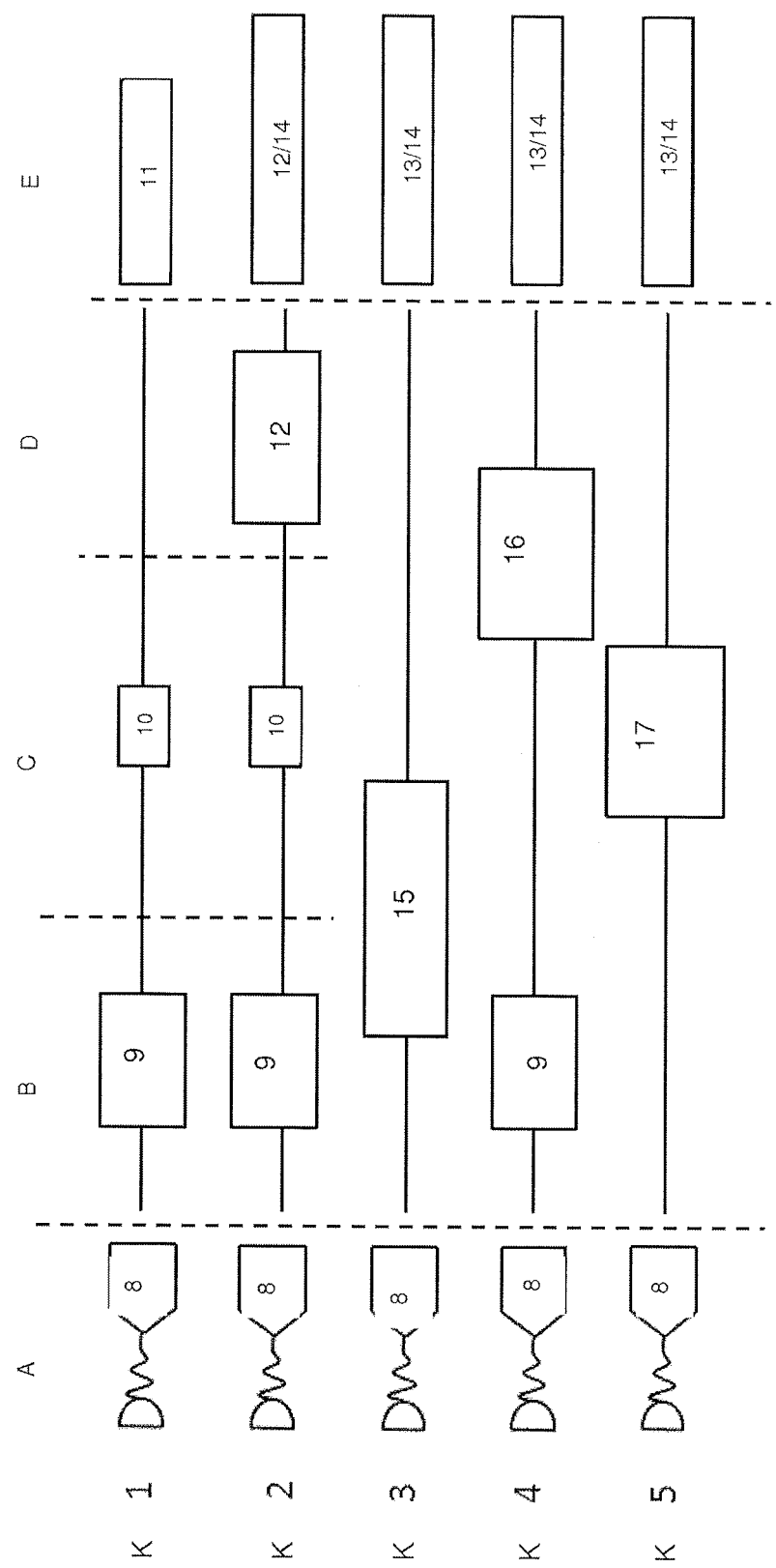
Figure 7:
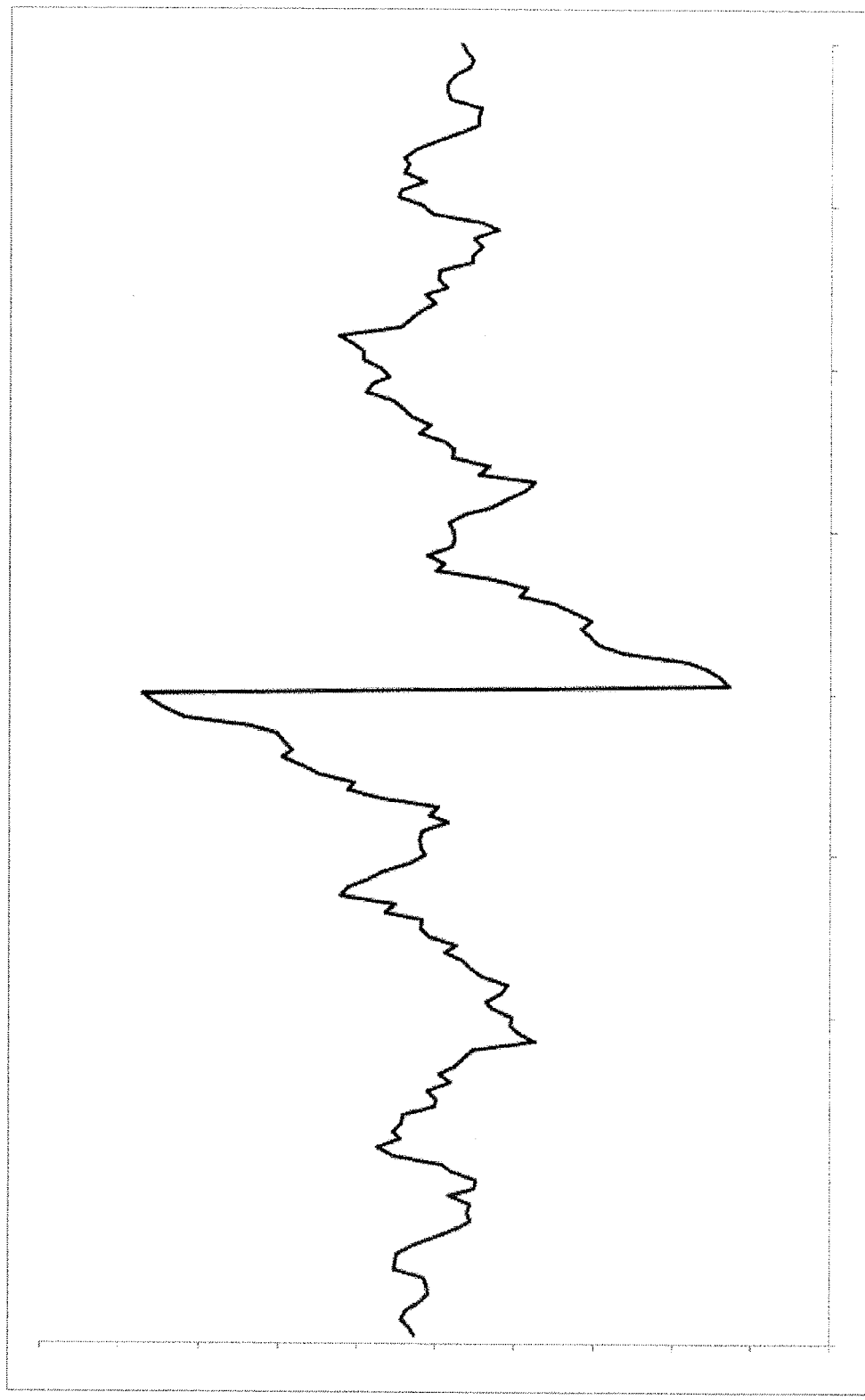
Figure 8:
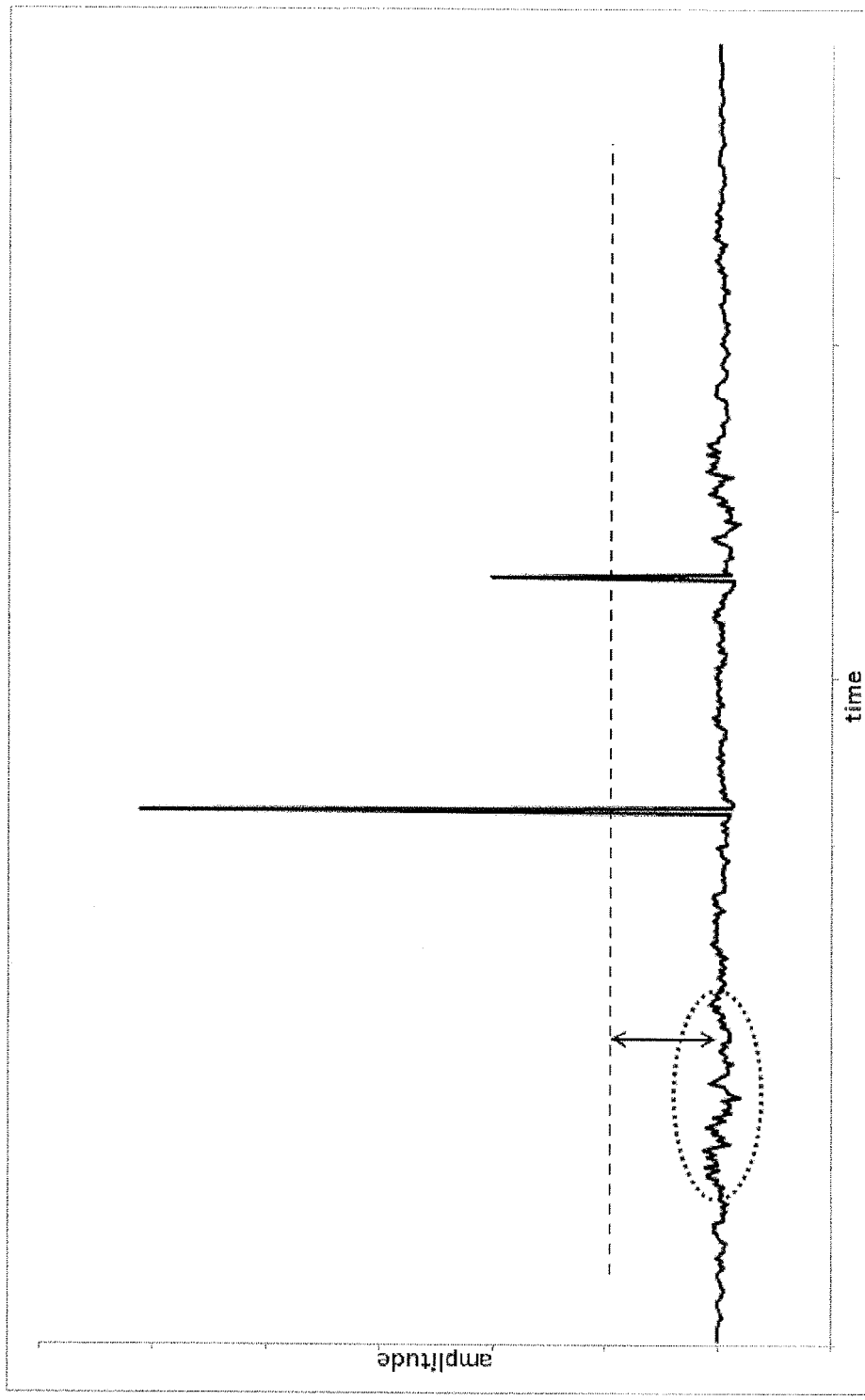
Figure 9:
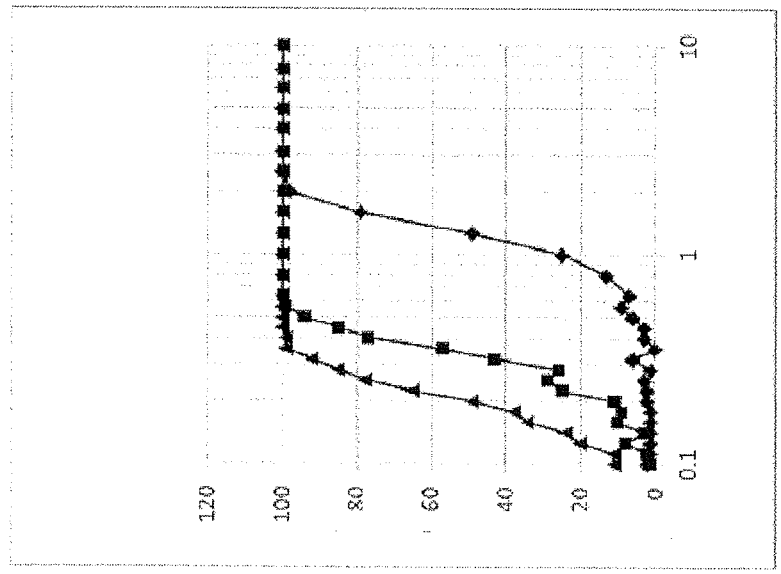
Figure 10:
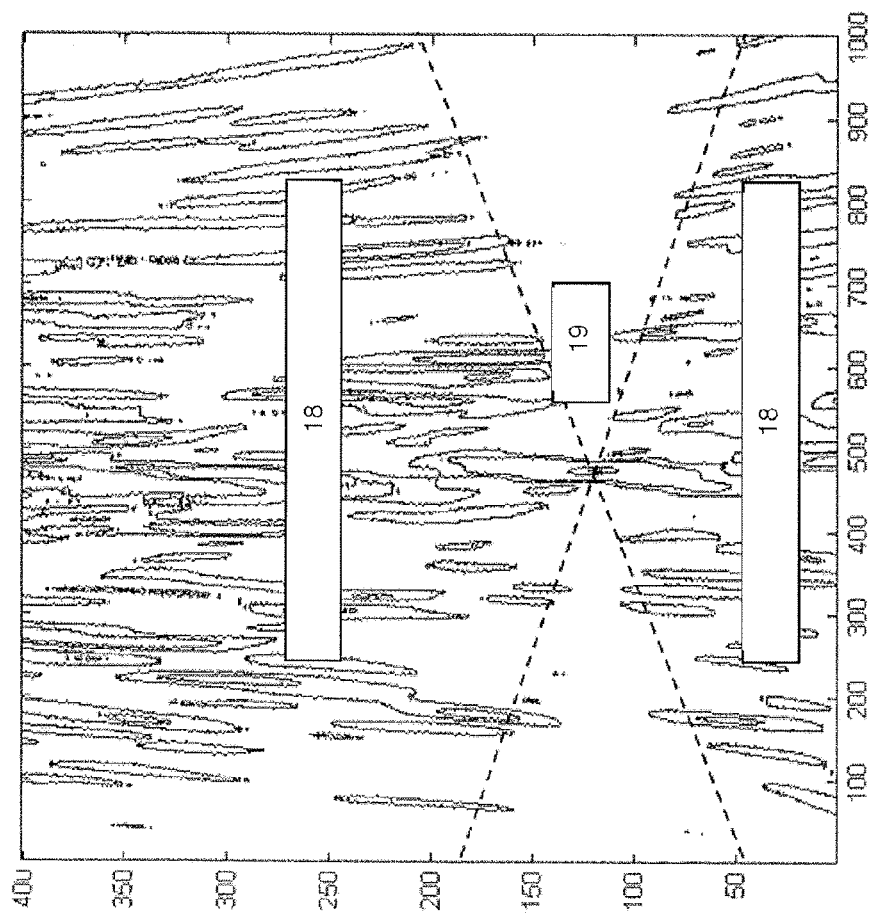
Figure 11:
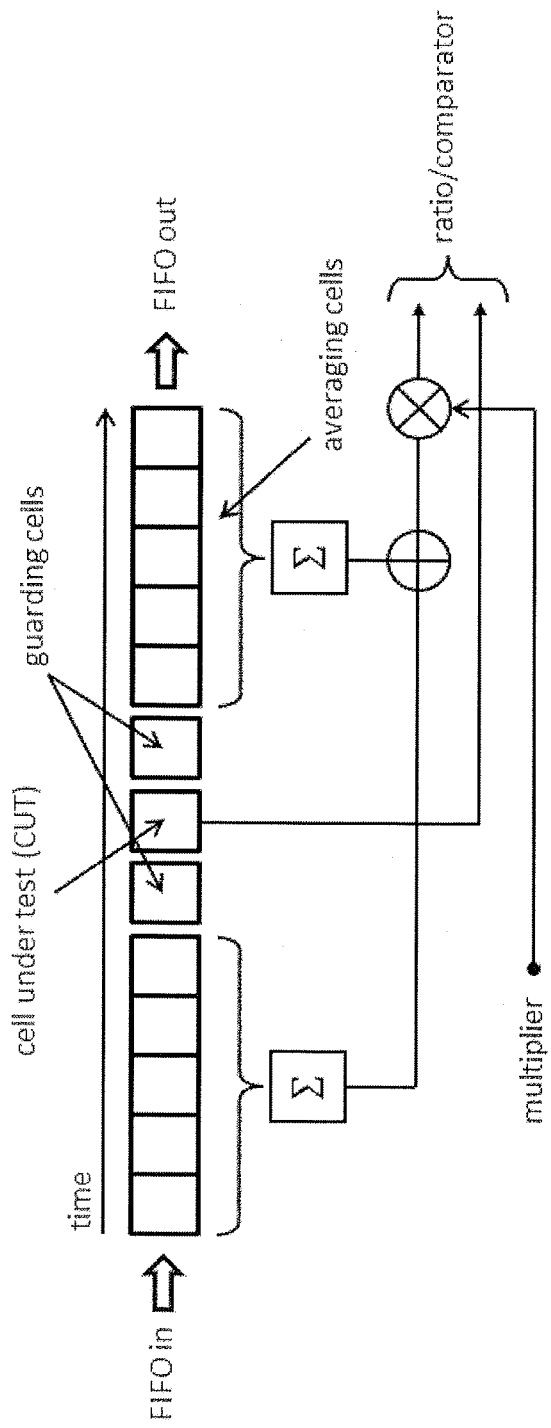
Figure 12:
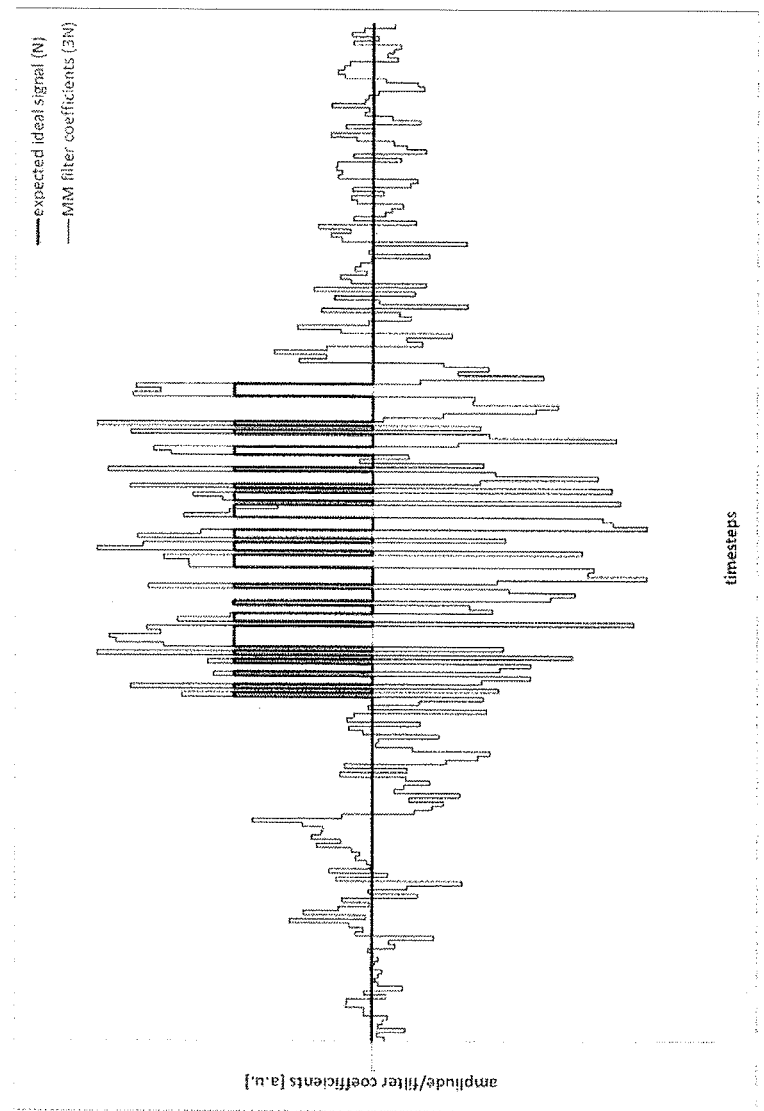
Figure 13:
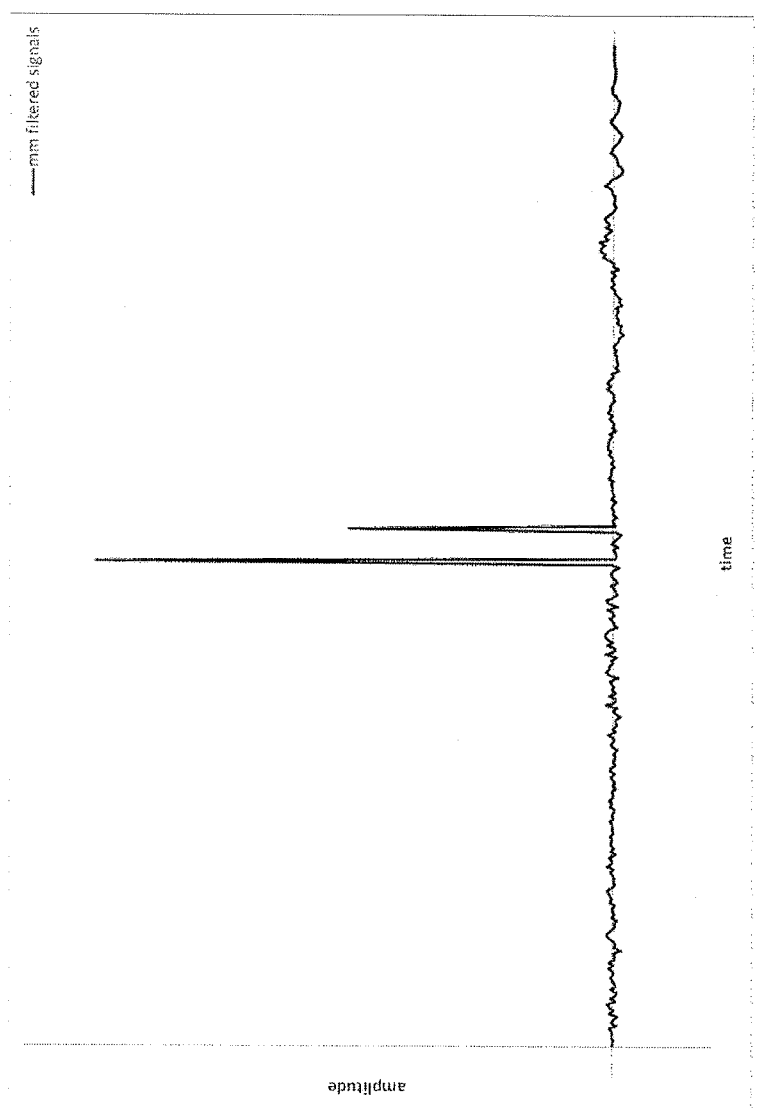
Figure 14A:
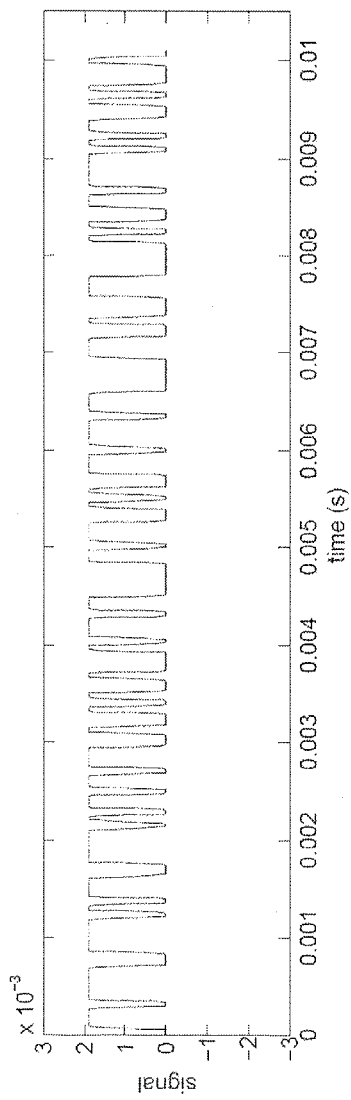
Figure 14B:
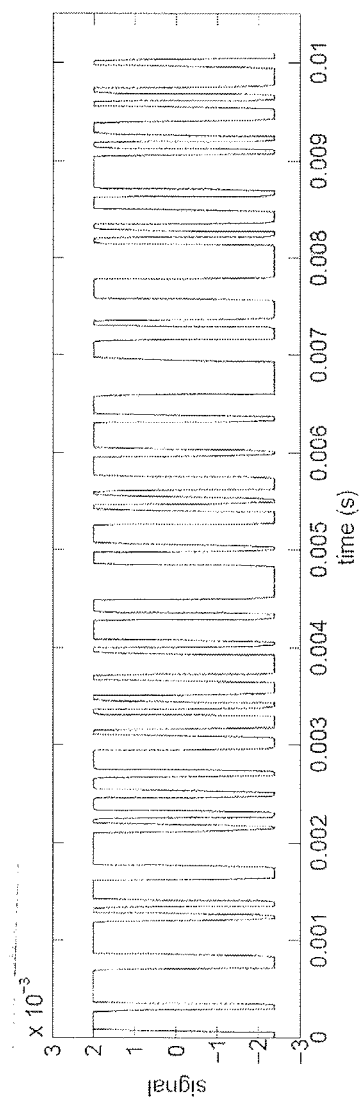
Figure 15:
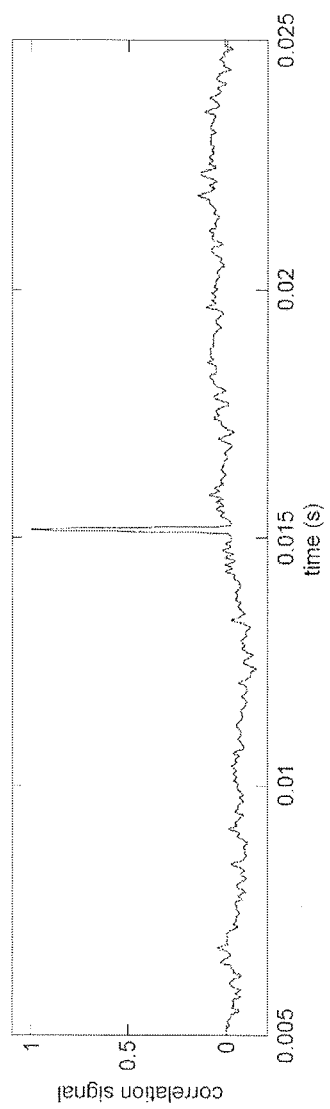

Further advantages, features and possible uses of the present invention will be clearly apparent from the description hereinafter of a preferred method and the accompanying Figures in which:

FIG. 1 shows a simplified form of a measurement signal with the amplitude 1 without noise and offset, FIG. 2 shows a simplified view of a superposed measurement signal, FIG. 3 shows the signal filtered with an optimum filter, FIG. 4 shows the differentiated signal of FIG. 3, FIG. 5 shows a diagrammatic cross-sectional view of a through-flow cytometer structure, FIG. 6 shows diagrammatic views of signal evaluation chains, FIG. 7 shows an example of optimized filter coefficients, FIG. 8 shows a signal filtered with a mismatched filter, FIG. 9 shows a simulation of the detection rates of a through-flow cytometer for different cases of signal production and evaluation, FIG. 10 shows a 2D view of a measurement by way of example, FIG. 11 shows a diagrammatic view of the CFAR principle, FIG. 12 shows a diagrammatic view of the expected signal and the filter coefficients for the signal evaluation chain K5, FIG. 13 shows a diagrammatic view of the signal filtered in accordance with signal evaluation chain K5, FIG. 14a shows the filter coefficients of an optimum filter, FIG. 14b shows the filter coefficients of an offset-correcting filter, and FIG. 15 shows the signal filtered by means of offset-correcting filters.

The method according to the invention is explained by reference to the example of a through-flow cytometer as is diagrammatically shown in FIG. 5. FIG. 5 shows a cross-section. The through-flow cytometer has a microchannel 2 which is mounted on a substrate 1 and through which fluorescing objects 3 are moved. In that situation they reach an excitation zone 4 which is illuminated by means for example of a laser beam whereby the objects are excited and emit fluorescing radiation. Provided in that region is an optical amplitude grating 5, that is to say a non-periodic binary filter 5, through which fluorescence radiation can issue, which passes by way of the optical filter 6 on to the detector 7. There substantially the signal shown in FIG. 2 above is received. The signal therefore comprises various rectangular pulses whose width corresponds to the width of the openings in the binary filter.

FIG. 6 diagrammatically shows 5 signal evaluation chains K1-K5. The first signal evaluation chain K1 describes the state of the art. The further signal evaluation chains K2-K5 are embodiments of the present invention.

The individual components of the signal evaluation chains can perform the following tasks: A: data acquisition, B: SNR optimization and pulse compression, C: offset elimination, D: sidelobe reduction, and E: particle detection.

What is common to all signal evaluation chains is an analog-digital converter 8 for data acquisition. The signal comprises individual measurement points $s_i$ which are continuously recorded at the time spacing dt. For signal processing, a portion of the length $N_j$ is removed from the signal after respective detection of a new measurement point k, wherein different $N_j$ can be selected for covering the particle transit time region. The signal portion at the moment in time $t_k$ is of the general form:

$$S_j(t_k)=S_{jk}=(s_{k-N_j+1}, s_{k-N_j+2}, \ldots, s_k)=B(t_k)+R(t_k)+A\cdot(m_{k-N_j+1}, m_{k-N_j+2}, \ldots, m_k)\ (m_i \in \{0,1\})).$$

Signal processing can begin as soon as the first $N_j$ measurement points have come in and the signal is thus completely present. The signal contains a noise component $(R(t_k)=(r_{k-N_j+1}, r_{k-N_j+2}, \ldots, r_k))$ and an offset component $(B(t_k)=(b_{k-N_j+1}, b_{k-N_j+2}, \ldots, b_k))$. As long as the offset component is constant in time then the following applies: $b_{k-N_j+1}=b_{k-N_j+2}=\ldots=b_k$. $A\cdot(m_{k-N_j+1}, m_{k-N_j+2}, \ldots, m_k)$ is the particle signal sought. At moments in time at which a particle is in front of an opening in the mask the particle delivers a contribution $m_k>0$. The prefactor A reproduces the amplitude of the particle signal.

Rounded-off configurations generally occur at the flanks of the signal due to the finite extent of the particles or objects and due to optical imaging on to the detector. In addition the amplitude can fluctuate along the signal as for example the excitation light is distributed non-homogenously in its intensity along the particle path. A diagrammatic view of a measurement signal in dependence on time without taking account of the noise and offset component is shown in FIG. 1.

As already described in the opening part of this specification it is known (K1) for the acquired data to be filtered by means of an optimum filter 9 in order to achieve pulse compression and to optimize the SNR.

For that purpose the signal can be for example correlated with an optimum filter whose filter coefficients exactly correspond to the expected ideal signal configuration. In other words the filter involves the general form:

$$F_j=K_j\cdot(f_{j1}, f_{j2}, \ldots, f_{jN_j}), (f_{ji} \in \{0,1\}),$$

If the filter is so selected that it corresponds to the exact signal configuration, the following applies: $f_i=m_i$. The calibration factor $K_j$ can be used to calibrate the amplitude resulting from the correlation on to the signal intensity. As the signal length is not necessarily known various filter lengths $N_j$ are "tried out". Correlation is effected according to the calculation rule:

$$C_j(t_k) = S_{jk} \times F_j = \sum_{i=1}^{N_j} s_{k-N_j+i} \cdot K_j \cdot f_{ji}$$

The filter lengths are tried out as there are different-length signal sequences, which is to be attributed to the differing speeds of the particles. For a fixed overall length of the physical modulation mask L and the sampling time $T_s$ a total length of the signal sequence $$M_j = \frac{L}{v_j \times T_s}$$

The fly-by time of a particle at a speed $v_j$ at a single opening is then given with $\tau_j$ and corresponds to a certain number of signal samples which is specific to that speed, physical mask length and sampling rate. The total observation duration for such a particle is then given with $$T_j=M_j T_s$$

The application of such a correlation procedure in conjunction with binary modulation sequences involves two essential reasons:
1) improvement to the signal-to-noise ratio (SNR),
2) pulse compression.

Regarding 1): as described above the overall signal which is present during the observation duration $T_j$ comprises the component of the actual signal, the (constant) offset and the noise amplitude with expectation value of 0 and given standard deviation $\sigma$. All signal components can be viewed as additive and the actual absolute signal component can be considerably smaller than the offset signal and the standard deviation of the noise amplitude. A quasi time-continuous correlation process then provides that, precisely when the signal is resonant (coincident) with the signal to be expected the time-distributed overall signal amplitude is weighted (that is to say by multiplication) integrated (totaled) $C_j(t_k)$: while a time-unchanged offset always delivers the same contribution $C_j^{off}(t_k)$ the correlation result the signal contribution varies according to how many "ones" ($m_m > 0$) of the modulation sequence are at that moment in time coincident with the corresponding filter coefficients. The actual useful signal therefore provides an alternating signal which is additively modulated to the correlated offset signal $C_j^{off}(t_k)$. As however considerable DC components are also contained beneath the useful signal the correlation process affords an additional offset component which is of a triangular shape and is characteristic of the respective modulation sequence (FIG. 3). The greatest deflection for the correlated useful signal is to be expected when the useful signal has completely come in and is coincident with the filter coefficients. The output voltage of the filter is then a measurement in respect of signal energy ($\overline{A}_j \times T_j$), which was deposited on the detector over the observation time. The noise signal on the other hand which has a time mean value of zero is severely damped by integration. That damping is correspondingly greater, the longer the integration operation takes place, that is to say the longer $T_j$. A long integration time $T_j$ which could also be achieved solely by the enlarged detection zone without modulation however would entail the disadvantage that the time/space resolution capability of the apparatus is worsened. For that reason special binary modulation sequences are used (instead of a single large opening) which during the correlation process additionally lead to pulse compression.

Regarding 2): as already explained in the case of an enlarged detection zone more fluorescence light, that is to say energy, is deposited on the detector. Due to integration that signal energy can then be rendered visible as before a superposed noise background and a particle signal can thus be detected while the noise amplitude in turn is damped. If the detection zone were steadily increased it would thus be possible to produce an SNR of any desired quality for individual particles. With an increase in the detection zone however the probability also rises that a plurality of particles can be present in the detection zone so that distinguishability between those particles becomes impossible as from a certain detection zone size. For that reason the detection zone is structured in addition, in accordance with a binary sequence, in which case as described above there are regions in which the fluorescence light is shadowed and those in which it is transmitted and can impinge on the detector. Those sequences are so optimized that a correlation process between useful signal and corresponding filter displays the full signal energy at the output only when the signal and the filter are in exactly time-coincident relationship. For all other moments in time the sequences are so selected that there is as little overlap as possible between the "ones" of the signal and the "ones" of the filter coefficients and the correlation signal is comparatively low. Nonetheless fluctuations cannot be entirely avoided and so-called signal sidelobes occur besides a characteristic triangular offset. For the moment in time of complete signal arrival and thus congruence of signal and filter a high deflection (peak) is nonetheless to be expected at the filter output, which stands out markedly from its environment. The time width of that peak corresponds in that case to precisely $\tau_j$, that is to say the time that the particle requires for passing a smallest mask opening. The smaller the structures of the shadow mask, that is to say the more ones and zeros occur on the length L the correspondingly sharper is the peak to be expected. That technique is referred to as pulse compression and is directly linked to the length of the selected binary sequence (the more openings occur on L, the correspondingly smaller become the openings and thus $\tau_j$. Summarized this means that upon pulse compression the signal energy which is initially distributed over the overall duration of the signal corresponding to the encoding is compressed into an individual pulse which is substantially shorter in time.

For various speed channels it happens that adjacent channels also trigger the effect of pulse compression. As the filter coefficients however become increasingly inappropriate (off-resonant) the signal amplitude at the filter output drops off rapidly with detuning. The channel which has the best fit therefore delivers the strongest correlation signal which is later selected for further processing.

It is further known for the signal processed by means of the optimum filter 9 to be derived 10 and for the result to be passed to particle detection 11 which uses a fixed threshold value.

The correlation signal obtained can be for example discretely derived in order to eliminate the offset $C_j^{off}(t_k)$ continued in the correlation signal and the triangular offset characteristic of the signal (FIG. 2):

$$dC_j(t_k) = C_j(t_k) - C_j(t_{k-1})$$

That delivers a characteristic signal form in which a maximum directly follows a minimum or vice-versa. The best fit between signal portion and assumed filter length $N_j$ delivers the strongest derived correlation signal which is therefore used for further processing, by applying for example a threshold value for particle detection.

According to the invention now a mismatched filter, that is to say a non-optimum filter, is used, which admittedly means that the signal-noise ratio is minimally worsened, but the detection rate is improved by a markedly enhanced peak-to-sidelobe dynamic.

In a first preferred embodiment (K3) therefore a filter is used whose filter coefficients are calculated from those of an optimum filter, insofar as the arithmetic mean of the filter coefficients of the optimum filter is subtracted from the filter coefficients of the optimum filter. That filter which is also referred to as an offset-correcting filter 15 also has negative filter coefficients. By that measure, it is possible to dispense with differentiation of the signal whereby the detection rate is markedly improved. The offset-correcting filter therefore performs tasks B and C (see signal evaluation chain K3 in FIG. 6).

FIG. 9 shows the percentage detection rate by way of the signal-noise ratio for measurements at the individual gap (♦), for measurements of the state of the art with a binary mask (■) and for measurements using an offset-correcting filter (▲). It will be seen that when using an individual gap structure the detection rate for signal-noise ratios of less than 2 markedly falls. By using the binary mask, even with a signal-noise ratio of 0.6 or better, a detection rate of almost 100% can still be achieved. If however the signal-noise ratio falls below 0.6 reliable detection no longer occurs.

By virtue of the use according to the invention of an offset-correcting filter however even with a signal-noise ratio of about 0.35 it is still possible to achieve a very high detection rate.

In a further preferred embodiment it is possible to dispense with the decision element 11 with the fixed threshold and instead the signal can be passed for further dynamic optimization to a mismatched filter 12 whose output is occupied by way of a CFAR element with an adaptive threshold value 13/14 (see signal evaluation chain K2 in FIG. 6).

In further embodiments it is also possible for the mismatched filter 12 of the signal evaluation chain K2 to be replaced by an offset-correcting mismatched filter 16 so that the differentiation operation can be omitted (signal evaluation chain K4) or for the mismatched filter 12 to be replaced by a mismatched filter 17 which also performs the task of the optimum filter 9 and the differentiation member 10 so that those elements can be eliminated (see the signal evaluation chain K5).

By way of example FIG. 12 shows for the method in accordance with the signal evaluation chain K5, both the amplitude of the expected signal and also the optimized filter coefficients in arbitrary units in relation to time. It will be seen that the filter is 3 times as long as the expected ideal signal. The ideal signal is of the length 81. The output signal filtered in that way is then shown in FIG. 13. The two particle peaks can be clearly seen. The sidelobes have been markedly suppressed.

To clearly illustrate the method in accordance with the signal evaluation chain K2 FIG. 14a shows the filter coefficients of an optimum filter suitable for a signal to be filtered. According to the invention however it is precisely the case that an optimum filter is not used, but for example an offset-correcting filter. The filter coefficients of such an offset-correcting filter are shown in FIG. 14b. The filter coefficients have been calculated from the filter coefficients of the optimum filter by subtraction of the geometrical mean of the filter coefficients of the optimum filter. When using the offset-correcting filter that gives the filtered or correlated signal shown in FIG. 15. A subsequent derivation step which still further increases noise can be avoided thereby.

The present invention came about during the development of a miniaturized through-flow cytometer. The core idea for particle identification in that case involves the use of a non-periodic binary mask, that is to say an amplitude grating, which provides for suitable amplitude modulation of the fluorescence light of excited particles. Particularly in the case of miniaturized objects signal preparation is particularly important by virtue of the low signal strength.

As already explained derived signals generally have strong signal sidelobes. They are specific in regard to intensity and speed of the passing particles. Basically therefore they can be referred to in their overall structure as the "fingerprint" of the particles. A simple overall (fixed) threshold value can basically be set to a preselected signal amplitude in such a way that it is possible to detect objects with corresponding signal energy. An overall threshold value however takes account only of the maximum amplitude but not the characteristic overall sequence of a particle.

According to the invention therefore the overall sequence, that is to say the complete "fingerprint" of the particle signal, is taken into consideration. That is effected by means of mismatched filters, that is to say for example with transversal filters with a finite pulse response.

As the autocorrelation signal of a binary signal is always of a length of 2N−1, wherein N is the length of the original binary signal, a time-continuous derivation of the signal again produces a signal of the length 2N. For further processing by a filter having regard to the characteristic overall signal therefore the length of a suitably adapted filter must correspond at least to the length of the signal to be treated. Longer filter structures which involve a multiple of that basic length can further improve the suppression of signal sidelobes. Hereinafter however by way of example a mismatched filter of the length 2N will now be described.

The detection of an object in sharp relationship in respect of time is linked directly to the degree of pulse compression. If that is increased by a longer binary code then on the one hand the spatial locational accuracy of the object in the channel is increased while on the other hand individual particles can be identified even in the presence of many other particles. In spite of the high level of time resolution the method according to the invention affords the advantage of being able to guarantee a high signal-noise ratio.

The filter output of the weighted mismatched filter should deliver for a specific input signal in the best-case scenario a delta-shaped output signal (sharply delimited in respect of time) with a comparatively great peak height (in relation to the sidelobes) and in a fixed ratio in respect of the peak height to the energy of the original signal.

In an embodiment therefore the weighted filter or its filter coefficients are determined by a procedure whereby firstly a test input signal is developed for a given particle speed, based on the binary mask used. That test signal is filtered by means of the digital filter and the filtered signal is optimized by varying the filter coefficients. Such optimization can be carried out in the form of a global optimization routine. Global optimization routines are always looking for the global minimum of a problem-specific minimization function and are implemented in many instances to avoid a convergence towards local minima. Minimization functions can be for example the sidelobe-to-peak ratio (PSLR)

$$PSLR = \frac{1}{R_0^2}(\max_{k \neq 0}|R_k|)^2$$

or the integrated sidelobe-to-peak-ratio (ISLR)

$$ISLR = \frac{1}{R_0^2}\sum_{k \neq 0} R_k^2$$

wherein $R_k$ denotes the time-discrete output signals of the prefiltered signal with fixed filter coefficients. $R_0$ is the value which occurs when the input signal in the time progression assumes the total filter length at the moment in time $t_0$.

For non-periodic rectangular patterns as usually occur in the through-flow cytometer it has been shown that the best results can be achieved with minimization of the ISLR.

Optimization can be carried out for example by means of the program LabView. FIG. 7 shows by way of example the optimized filter coefficients (Y-axis) for a weighted filter for a derived correlation signal of the length 162 (original binary signal of the length 81). (The original binary signal corresponds to the signal shown in FIG. 12.) Here too there are 162 coefficients (=2M). It will be immediately seen that the filter coefficients deviate completely from the mathematical representation of the binary mask. The associated signal processing path is path 2 in FIG. 6.

As already stated above the decisive reason for developing an enlarged signal process chain is the threshold value problem for a multiparticle signal. The view shown in FIG. 8 qualitatively shows how a weighted filter acts on the signal shown in FIG. 2. It will be seen that, from the amplitude of the main peak, after application of the weighted digital filter, particle intensity can be obtained from the filter coefficients used. It can already be seen here that the sidelobes are markedly suppressed so that the risk of too many false events being detected or events with a low level of radiation intensity being overlooked is minimized.

In practice however, because of their differing size and the flow profile in the microchannels, the particles involve different speeds. In accordance with the maximum speed to be expected therefore the sampling rate of the analog-digital converter has to be adapted to be able to suitably quantize the speed range. That also permits a high degree of flank steepness of the binary-modulated measurement signal and thus a high level of time resolution. In that case the binary code can stretch to between many 100 and 1000 enquiries for a particle, which requires many filter channels matched to the respective total number of enquiries. While a binary signal can be easily compressed and stretched a filter which generally contains rational values in broken form has to be suitably extrapolated to the measurement signal locations. Linear extrapolation has proven to be the best variant for the specific case here.

To resolve the problem of differing speeds therefore weighted digital filters have been developed for a large number of different speeds and same are used in different speed channels. In that case—as described above—optimization for each individual mismatched filter can be effected separately. Alternatively—and preferably in most cases—the appropriate mismatched filter can be determined only for one particle speed by means of the described optimization process and the mismatched filters for the other particle speeds are determined from suitable extrapolation of the filter coefficients. More specifically it has been shown that, by compressing or stretching a filter which is optimized for a particle speed, almost optimized filters for other particle speeds can be acquired. That markedly reduces the computing involvement necessary for optimization.

FIG. 10 shows the output of a weighted filter on 400 speed channels (y-axis) for a one-particle signal. Time is plotted in the x-direction. Basically the same time measurement signal is processed in 400 different speed channels with 400 different weighted digital filters. The corresponding evaluation results are shown in FIG. 10. In fact most filters are not adapted to the particle speed (that is to say they are not resonant in relation to the speed) and they therefore lead to signals with a heavy background. These can be seen in the regions identified by reference 18.

The so-called "mismatched"-filtered signals involve a certain interference structure. As can be clearly seen from FIG. 10, that structure narrows towards the actual particle position 19 until it finally almost disappears. It is thus already possible to see from FIG. 10 that the detected particle involves a particle speed substantially corresponding to the speed to which the mismatched filter used in speed channel 125 was adapted.

That form can be utilized for a CFAR detector.

A CFAR detector substantially comprises a certain number of memory cells which function as "first in-first out" memories (FIFO), similarly to a digital transversal filter. In that respect various functions are allocated to the cells involved: 1st cell being tested ("cell under test" or "CUT"), 2nd guide cells ("guarding cells") and 3rd average cells ("averaging cells").

The tested cell is the middle cell. Its content is compared to the outer cells. The cells which are directly around the middle cell are not used for calculation purposes. These are the so-called guarding cells, the number of which towards each side approximately corresponds to half the peak width in samples. In dependence on implementation comparison by a comparator and thus the formation of a dynamic threshold value can be effected in different ways: thus for example an averaging CFAR (CACFAR) or an ordered statistic CFAR (OSCFAR) can be used. A further variant of the CACFAR is the CAGOCFAR, wherein "GO" stands for "greatest of". That CFAR variant functions similarly to the CACFAR but in addition is capable of making a distinction between preceding and premature signals in respect of time, which are then compared to the value of the CUT.

While the first variant of the detector compares the multiplicatively weighted average of all outer cells to the value of the cell under test, by for example relating them together, OSCFAR initially involves sorting of the amplitude values in respect of their magnitude. Then the value of a previously established statistical range of the sorted values is compared to the value of the cell under test. The principle is shown in FIG. 11. As a sorting operation is time-consuming the CACFAR variant is easier to implement and is discussed in greater detail hereinafter.

In the CACFAR checking for a valid signal peak is effected mathematically by way of a comparison of the CUT with the weighted value of the averaging cells in accordance with the rule:

$$\text{CUT} \geq a \times \Sigma_{averagingcells}$$

With the weighting factor a.

If a valid peak signal passes through the filter structure and if the speed channel is resonant with the particle speed, that is to say the particle speed to which the digital filter on the speed channel is adapted corresponds to the actual particle speed, the comparator will deliver a deflection for a found particle as then there are scarcely any signal components in the outer cells. For a non-resonant channel in contrast there are strong signal sidelobes in the averaging cells and the comparator will not detect the particle in such a channel. Strong waviness on non-resonant channels will therefore not result in detection on such a channel.

Alternatively that decision criterion can also be brought about when only one side of the CFAR fulfills that condition (CAGOCFAR). That separate consideration can lead to better detection information if for example there is a second peak in the region of the averaging cells.

The decision criterion of the CFAR processor will always relatively occur depending on the respective signal strength as high signals have high sidelobes and low signals have small sidelobes. By virtue of a weighted comparison of the peak (CUT) with the weighted mean value of its characteristic sidelobes (CACFAR) it is therefore not the absolute signal amplitude that is discriminated, but the configuration of the signal ("fingerprint"). In other words the CFAR principle allows dynamic threshold value formation precisely when an optimum or approximately optimum filter result is achieved on a resonant channel.

In that way a possible procedure for dynamic detection limit adapted to the signal energy is attained.

What is common to all CFAR methods is that, by way of the comparison of the CUT with its environment, they can provide for relative information about a valid particle signal (particle potentially present or not). As that can be effected on a plurality of channels and at a plurality of moments in time around the actual peak (in dependence on the number of averaging/guarding cells and weighting factor), the array of correlation signals in that region must be subsequently searched for the actual maximum in order to discover the actual peak position in respect of time and in the speed channel.

For example the CFAR presents a valid signal at the moments in time $t_k$ -$t_{k-5}$ on the speed channels $v_{j-2}$ -$v_{j+2}$. Overall therefore 25 different values are involved (($t_k$, $v_{j-2}$), ($t_k$, $v_{j-1}$), -($t_{k-5}$, $v_{j+2}$)) at which the actual peak is to be found. An immediate or subsequent maximum search on all channels or only in that portion of the correlation data is therefore essential for determining both moment in time, amplitude and speed of the particle with the best possible accuracy.

The invention claimed is:

1. A method of detecting particles, that move along a trajectory and that produce, or at least influence, electromagnetic radiation, an electrical field or a magnetic field, wherein the electromagnetic radiation, the electrical field or the magnetic field is detected, in which a structuring device is used, that either ensures that the particles along the trajectory produce or at least influence the electromagnetic radiation, the electrical field or the magnetic field substantially only at non-periodic spatial spacings, or ensures that the electromagnetic radiation, the electrical field or the magnetic field is detected substantially only at non-periodic spatial spacings along the trajectory, wherein a detected signal S is processed by a mismatched filter $F_1$ and, if a signal $D_{F1}(S)$ filtered in that way fulfills a predefined threshold criterion, a particle is detected, and, if the signal filtered in that way does not fulfill the predefined threshold criterion, no particle is detected, wherein filter coefficients of the mismatched filter are calculated from filter coefficients of an optimum filter so that the mismatched filter has the filter coefficients of the optimum filter, that are reduced by a predetermined value and wherein the predetermined value is substantially equal to the arithmetic average of all filter coefficients of the optimum filter.

2. The method according to claim 1, wherein a non-periodic structured mask is used as the structuring device and the particles are moved past one side of the mask at a speed v and the electromagnetic radiation passing through the mask, the electrical or the magnetic field is detected on the other side.

3. The method according to claim 2, wherein the mismatched filter $F_1$ is adapted to a particle speed $v_1$ and to the non-periodic structured mask, wherein in the case of processing with a plurality of digital mismatched filters ($F_i$, i=1,2, . . . ) each digital mismatched filter ($F_i$, i=1,2, . . . ) is adapted to the non-periodic structured mask and to a particle speed $v_i$, wherein each mismatched filter ($F_i$, i=1,2, . . . ) is adapted to another particle speed $v_j (j \neq i)$.

4. The method according to claim 3, wherein when a particle is detected a speed v thereof is approximately determined by the speed v relative to $v_{Best}$ being determined, wherein $v_{Best}$ is the particle speed to which the digital mismatched filter $F_{Best}$, which supplies the best digitally filtered signal $D_{Fbest}$ is adapted.

5. The method according to claim 1, wherein the detected signal S is processed by a plurality of different mismatched filters ($F_i$, i=1,2, . . . ) to produce a plurality of digitally filtered signals $D_{Fi}(S)(i=1,2, . . .)$, that a best digitally filtered signal $D_{Fbest}$ is selected from the plurality of digitally filtered signals $D_{Fi}(S)(i=1,2, . . .)$ by a predetermined selection criterion and if the best digitally filtered signal $D_{Fbest}$ fulfills a predefined threshold criterion a particle is detected and if the best digitally filtered signal $D_{Fbest}$ does not fulfill the predefined threshold criterion no particle is detected.

6. The method according to claim 5, wherein a predetermined selection criterion uses a Constant False Alarm Rate (CFAR), an Ordered Statistic CFAR (OSCFAR), or a Cell-Averaging Greatest of CFAR (CAGOCFAR).

7. The method according to claim 5, wherein $v_i$ is selected as $<v_{i+1}$, that a subgroup of digital mismatched filters ($F_i$, i=(k+c×i)) with a constant k and a factor c is selected from the plurality of different mismatched digital filters ($F_i$, i=1,2, . . . ) and the detected signal S is processed by the subgroup of different digital mismatched filters ($F_i$, i=1,2, . . . ) to produce a plurality of digitally filtered signals $D_{Fi}(S)(i=1,2, . . .)$, that a best digitally filtered signal $D_{Fbest}$ is selected from the plurality of digitally filtered signals $D_{Fi}(S)(i=1,2, . . .)$ by a predetermined selection criterion, and in a further step a further subgroup of digital mismatched filters ($F_i$, i(best−c . . . best+c)) is selected, whose elements were ascertained on the basis of particle speeds which are in a predetermined interval around the particle speed at which the selected best filter was determined, that the processing step and the selection step are carried out again using the further subgroup and if the best digitally filtered signal $D_{Fbest}$ fulfills a predefined threshold criterion a particle is detected and if the best digitally filtered signal $D_{Fbest}$ does not fulfill the predefined threshold criterion no particle is detected.

8. The method according to claim 1, wherein a length of the mismatched filter or filters is at least M, wherein M is the length of the signal to be filtered by mismatched filters.

9. The method according to claim 8, wherein the length of the mismatched filter is greater than M.

10. The method according to claim 9, wherein the length of the mismatched filter is a maximum of 3M.

11. The method according to claim 1, wherein the mismatched filter or filters is or are ascertained by optimization of a digitally filtered test signal, wherein a signal to be expected for a particle speed $v_i$, and a binary mask used is created and used as the test signal.

12. The method according to claim 11, wherein at least one first mismatched filter having filter coefficients adapted to a particle speed is determined by optimization and at least one second mismatched filter adapted to another particle speed is determined by extrapolation or interpolation of the filter coefficients of the first mismatched filter.

13. The method according to claim 11, wherein the mismatched filter or filters is or are ascertained by a minimization of a sidelobe-to-peak-ratio (SPLR) or a minimization of an integrated sidelobe-to-peak-ratio (ISLR) of the digitally tested signal.

14. The method according to claim 13, wherein the ascertaining operation is effected by way of the minimization of the minimum integrated sidelobe-to-peak-ratio (ISLR).

15. The method according to claim 1, wherein the detected signal S is firstly prefiltered with an optimum filter and then processed with the digital mismatched filter.

16. The method according to claim 15, wherein the prefiltered signal is derived in respect of time and then processed with the digital mismatched filter.

* * * * *